(12) United States Patent
Horn et al.

(10) Patent No.: US 12,157,176 B2
(45) Date of Patent: Dec. 3, 2024

(54) TEMPERATURE MONITORING AND INDICATOR SYSTEM FOR A CAST SAW

(71) Applicant: The Children's Hospital of Philadelphia, Philadelphia, PA (US)

(72) Inventors: Bernard David Horn, Wynnewood, PA (US); John Todd Rutter Lawrence, Wynnewood, PA (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 250 days.

(21) Appl. No.: 17/763,903

(22) PCT Filed: Sep. 25, 2020

(86) PCT No.: PCT/US2020/052834
§ 371 (c)(1),
(2) Date: Mar. 25, 2022

(87) PCT Pub. No.: WO2021/062233
PCT Pub. Date: Apr. 1, 2021

(65) Prior Publication Data
US 2022/0402049 A1    Dec. 22, 2022

Related U.S. Application Data

(60) Provisional application No. 62/906,401, filed on Sep. 26, 2019.

(51) Int. Cl.
*B23D 59/00*   (2006.01)
*A61F 15/02*   (2006.01)
*B23D 45/16*   (2006.01)

(52) U.S. Cl.
CPC ............ *B23D 59/001* (2013.01); *A61F 15/02* (2013.01); *B23D 45/16* (2013.01)

(58) Field of Classification Search
CPC ........ B23D 59/001; B23D 45/16; A61F 15/02
(Continued)

(56) References Cited

U.S. PATENT DOCUMENTS

2006/0159533 A1   7/2006   Zeiler et al.
2016/0263762 A1*  9/2016   Ramaswamy ........... B26D 7/22
(Continued)

FOREIGN PATENT DOCUMENTS

CN         106353006 A      1/2017

OTHER PUBLICATIONS

International Preliminary Report on Patentability and Written Opinion for International Application No. PCT/ JS2020/052834, issued Mar. 15, 2022, 12 pages.
(Continued)

*Primary Examiner* — Omar Flores Sanchez
(74) *Attorney, Agent, or Firm* — Buchanan Ingersoll & Rooney PC

(57) ABSTRACT

A power tool, such as a cast saw is disclosed. The cast saw is equipped with at least one thermocouple and and/or at least one infrared detector that measure the temperature of the cutting blade on the cast saw or the area in the cast immediately surrounding the cutting blade. The cast saw is also equipped with at least one LED that can alert a user of the cast saw when blade or the area in the cast immediately surrounding the blade is approaching or has reached a temperature that may burn a patient. Also disclosed is a shroud for the cutting blade of the cast saw. The shroud not only surrounds at least part of the blade but also houses the thermocouple or infrared detector and the LEDs(s). A method of operating the cast saw to cut a cast off of a patient is also disclosed.

25 Claims, 15 Drawing Sheets

(58) Field of Classification Search
USPC .............................................................. 83/13
See application file for complete search history.

(56) References Cited

U.S. PATENT DOCUMENTS

| | | | | |
|---|---|---|---|---|
| 2017/0274489 | A1* | 9/2017 | Baratta | B23Q 17/0985 |
| 2019/0183696 | A1 | 6/2019 | Halanski et al. | |
| 2020/0276661 | A1* | 9/2020 | Bylund | B23Q 11/1092 |
| 2022/0097155 | A1* | 3/2022 | Vogt | G01K 13/08 |
| 2023/0398614 | A1* | 12/2023 | Vandenbush | B23D 59/02 |

OTHER PUBLICATIONS

Halanski, M., "How to Avoid Cast Saw Complications," Journal of Pediatric Orthopaedics, vol. 36, No. 4, Supplement 1, Jun. 2016, 5 pages.

International Search Report and Written Opinion for International Application No. PCT/US2020/052834, dated Dec. 21, 2020, 12 pages.

Leopold, S., "Editor's Spotlight/Take 5: To Cast, to Saw, and Not to Injure: Can Safety Strips Decrease Cast Saw Injuries?," Clinical Orthopaedics and Related Research®, vol. 474, No. 7, Feb. 28, 2016, pp. 1538-1542.

* cited by examiner

TEMPERATURE MONITORING AND INDICATOR SYSTEM FOR A CAST SAW

CROSS-REFERENCE TO RELATED APPLICATIONS

This is a U.S. National Phase Application of international application number PCT/US2020/052834, filed Sep. 25, 2020, which claims priority from U.S. Provisional Application No. 62/906,401, filed on Sep. 26, 2019, the entire disclosure of each of which are incorporated by reference herein for all purposes.

FIELD

The present subject matter relates to a temperature monitoring and indicator system for a power tool, for example a cast saw.

BACKGROUND

Since 1945, medical cast saws have utilized high-frequency, small-amplitude, blade oscillation to cut through cast material [Halanski, Matthew A. "How to Avoid Cast Saw Complications." *Journal of Pediatric Orthopaedics*, vol. 36, June 2016, doi:10.1097/bpo.0000000000000756]. The nature of the small-amplitude oscillating blade theoretically prevents injury to the patient by allowing soft tissue to move back and forth with the blade, dissipating the shear forces. Since the cast itself is not soft, the oscillation of the blade wears though the much stiffer cast material, thereby cutting through the cast, in theory without injuring the patient. However, in practice, there is a probability of thermal and abrasive injuries caused by the cast saw blades which have medico-legal costs averaging $445,144 per year, or $15,898 per patient [Leopold, Seth S. "Editor's Spotlight/Take 5: To Cast, to Saw, and Not to Injure: Can Safety Strips Decrease Cast Saw Injuries?" *Clinical Orthopaedics and Related Research®*, vol. 474, no. 7, 28 Feb. 2016, pp. 1538-1542, doi:10.1007/s11999-016-4808-1].

Human factors are a primary source of injury, such as user error and patient factors. User error depends on the number of times the blade touches the skin and patient factors depend on the patient's ability to communicate with the healthcare provider. Young and non-verbal patients are not always able to communicate to the medical professional operating the saw that the cutting activity is causing discomfort prior to causing an injury. Although abrasive injuries occur three times more often than thermal injuries, they depend greatly on human factors that can be changed with adequate training.

The thermal injuries also depend on material behavior [Halanski], in addition to the human factor, and therefore are not completely mitigated by training. In particular, the high-frequency oscillation of the blade against the cast material causes both the blade and the cast itself that is in immediate proximity to the moving blade to heat up due to friction. Since the material of the cast is typically a poor conductor of heat, both the blade and the portions of the cast in close proximity to the blade, i.e. the freshly cut surface, become hot. This heat does not dissipate quickly because the cast material is a poor heat conductor. Thus, patients lacking adequate communication ability may suffer a burn along the cutting line during the cast removal process.

Therefore, there is a clear need for a cost-effective and easy to use warning system for the medical practitioner that can alert them that the cast, particularly the freshly cut surface thereof and/or cutting blade, are becoming dangerously hot so that the cutting operation can be paused, allowing the blade and cast to cool, before a patient is injured.

SUMMARY

Disclosed herein are power tools operable by a user. In one embodiment, a power tool has a cutting device which has a temperature. The power tool also has a data generating module, which is configured to generate data correlative to the temperature of the cutting device. The power tool additionally has a data collection and processing module which is configured to both collect the data correlative to the temperature of the cutting device, and also to process the data correlative to the temperature of the cutting device to determine the temperature of the cutting device. Finally, the power tool has a temperature notification module which is configured to both receive the temperature of the cutting device from the data collection and processing module, and also to produce a temperature output that can be detected by the user.

Also disclosed herein are shrouds for cutting blades of power tools. In one embodiment, a shroud has a first housing portion for the cutting blade. The shroud also has a second housing portion for a data generating module. The data generating module is configured to generate data correlative to a temperature of the cutting blade. Finally, the shroud has a third housing portion for a temperature notification module. The temperature notification module is configured to produce a temperature output that can be sensed by a user of the power tool.

Methods of operating a cast saw to cut a cast off of a patient are also disclosed.

In one method, a first step is to provide a cast saw. The cast saw comprises a cutting device having a temperature and a data generating module which is configured to generate data correlative to the temperature of the cutting device. The cast saw also comprises a data collection and processing module which is configured to both collect the data correlative to the temperature of the cutting device, and to process the data to determine the temperature of the cutting device. The cast saw also has a temperature notification module which is configured to receive the temperature of the cutting device from the data collection and processing module. The temperature notification module also produces a first temperature output corresponding to a safe temperature of the cutting device, and a second temperature output corresponding to an excessive temperature of the cutting device. The first output and the second output can be detected by a user of the cast saw. Finally, the cast saw also has an ON/OFF switch.

A second step of the method is detecting that the temperature notification module is producing the first temperature output and is not producing the second temperature output.

If the first temperature output is detected, a third step is turning the ON/OFF switch to ON and operating the cast saw to cut the cast.

Finally, a fourth step is turning the ON/OFF switch to OFF when the cast is completely cut, or when the second temperature output is detected.

BRIEF DESCRIPTION OF THE DRAWINGS

The present disclosure may be better understood by referring to the following drawings.

DETAILED DESCRIPTION

In the following detailed description, numerous specific details are set forth by way of descriptions of certain embodiments and by way of examples in order to provide a thorough understanding of the relevant teachings. However, it should be apparent to those skilled in the art that the present teachings may be practiced without such details. In other instances, well known methods, procedures, compounds, and/or compositions have been described at a relatively high-level, without detail, in order to avoid unnecessarily obscuring aspects of the present teachings.

Figure 1:
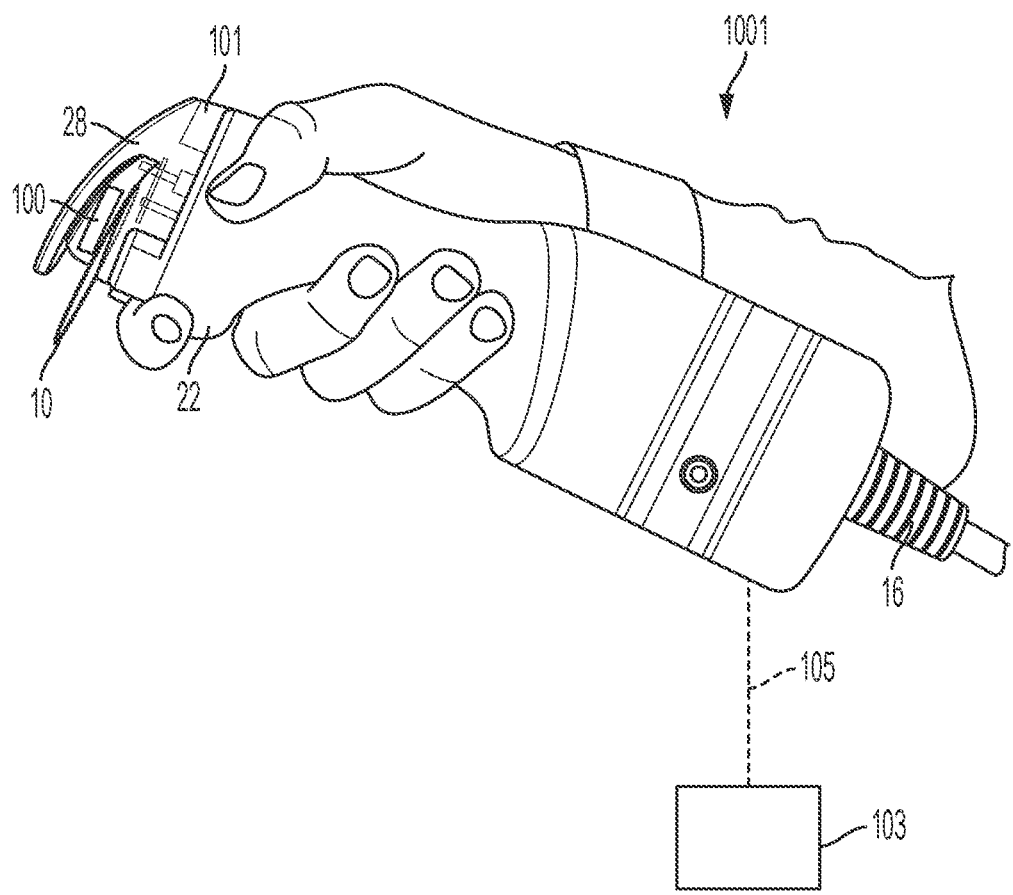
FIG. 1 shows an exemplary embodiment of the cast saw.
Figure 2:
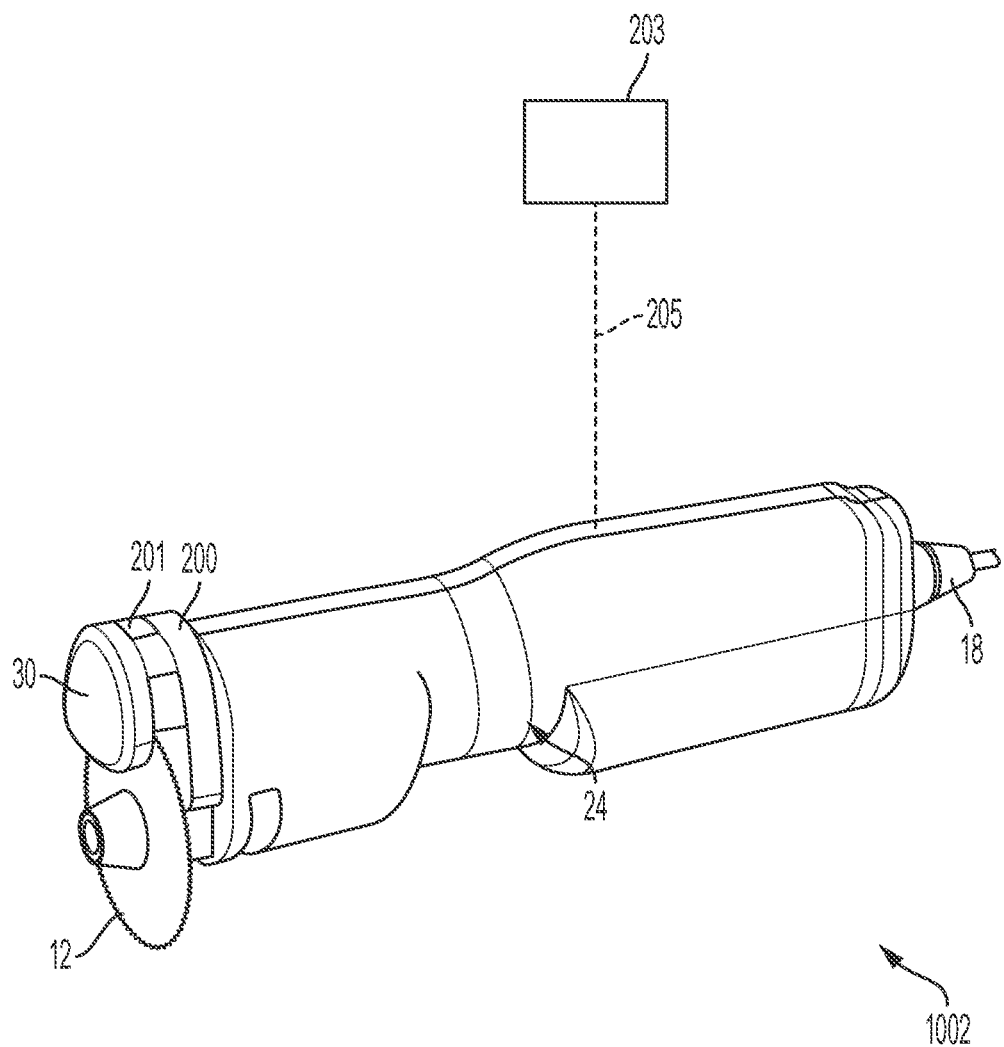
FIG. 2 shows another exemplary embodiment of the cast saw.
Figure 3:
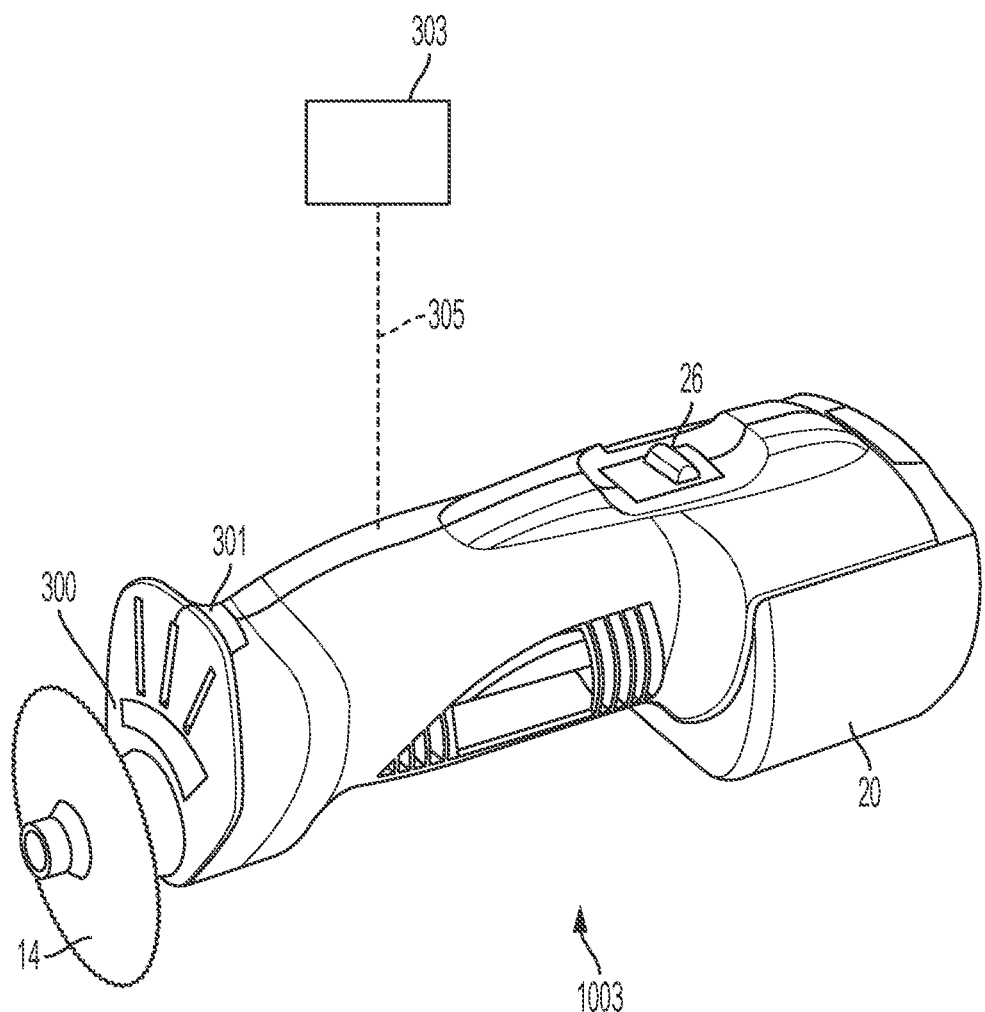
FIG. 3 shows yet another exemplary embodiment of the cast saw.

FIGS. 1, 2 and 3 show three non-limiting embodiments 1001, 1002, and 1003, respectively, of hand-held power tools that may be used to remove casts, i.e. cast saws. All of these three embodiments comprise at minimum, a cutting device in the form of a blade or cutting blade, 10, 12, 14. The cutting blades 10, 12, 14 may be formed of any suitable material, but generally are made of metal. Non-limiting examples of suitable blade materials are stainless steel, ion nitride treated metal, and titanium nitride, either as the blade material itself or as a coating on another material to impart durability. The cast saws 1001, 1002, 1003 each have a power supply 16, 18, 20. The power supplies may be in the form of an electric cord 16, 18, or a battery 20, or combinations thereof. The battery 20 may be disposable or rechargeable. All of the cast saw exemplary embodiments 1001, 1002, 1003 have an ON/OFF switch 22, 24, 26. The cast saws 1001, 1002 may have a blade cover or hood or shroud 28, 30 that covers at least a part of the blade 10 or 12 respectively as shown in FIG. 1 and FIG. 2. These shrouds are typically removable.

Figure 16:
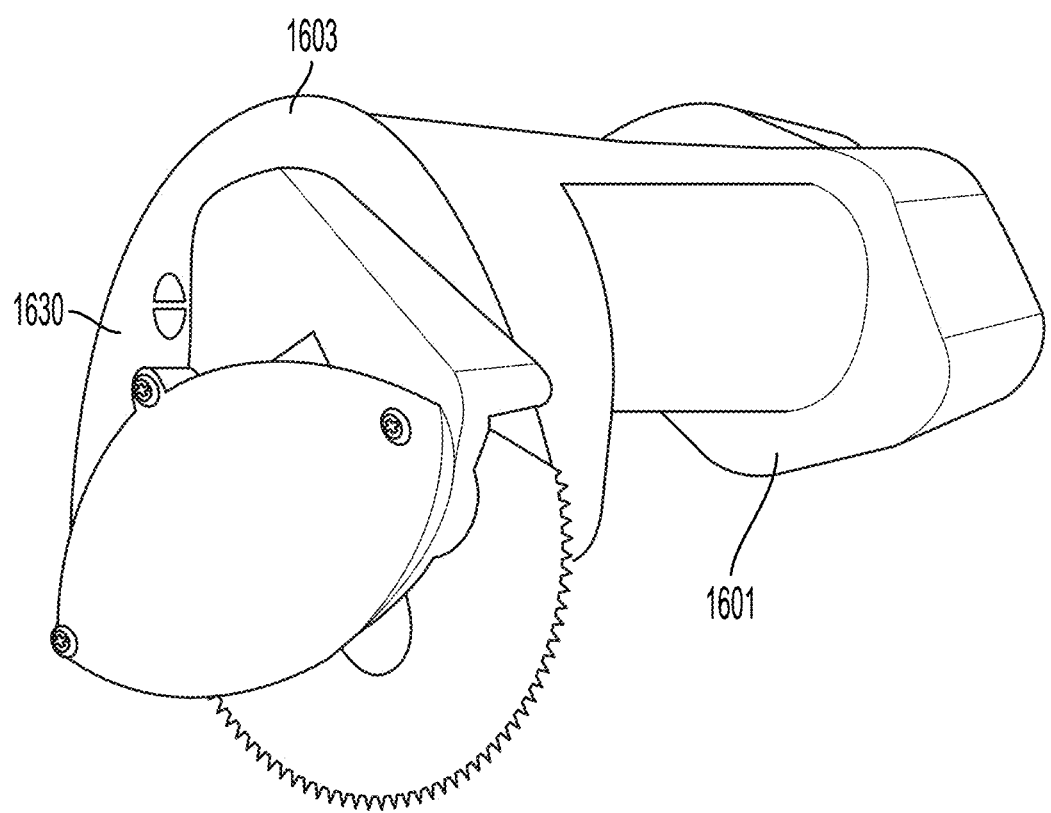
FIG. 16 shows yet another exemplary embodiment of the cast saw.

FIG. 16 shows another exemplary embodiment 1601 of the cast saw. It may be seen in this embodiment that a portion of the shroud 1630 is translucent. This provides the ability for an LED 1603 to be completely encased in the shroud, while remaining visible.

Figure 17:
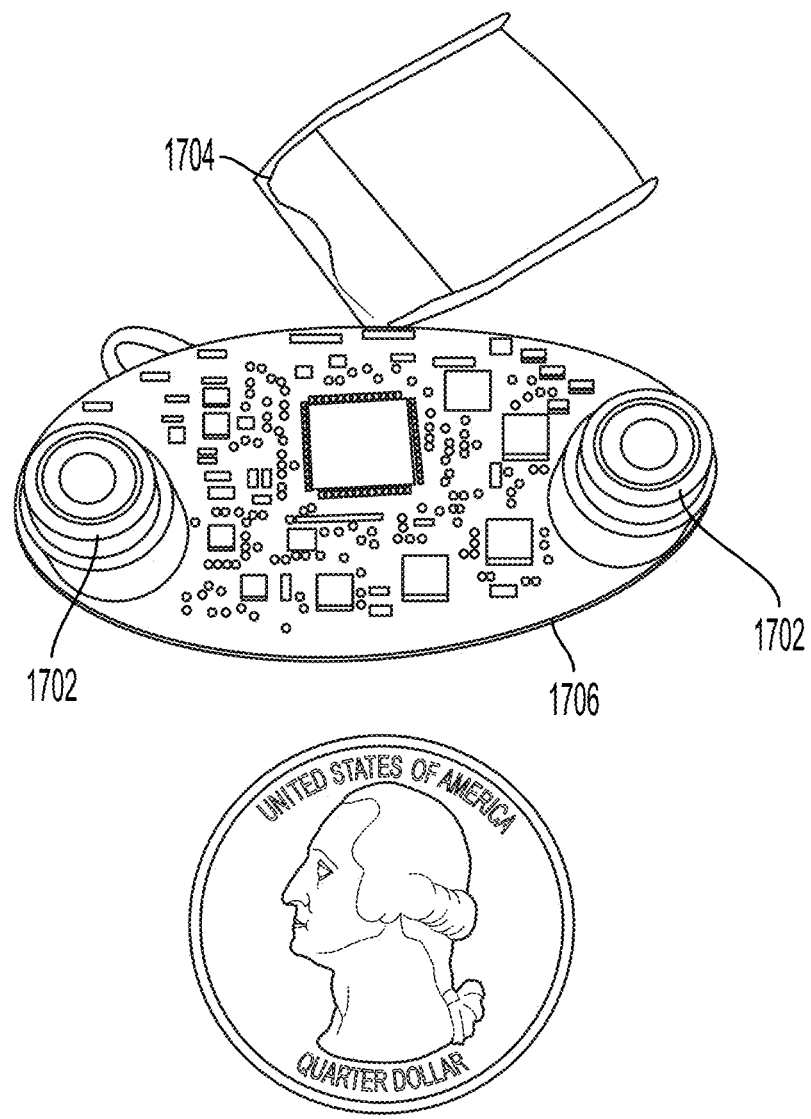
FIG. 17 is photograph of an exemplary infrared detector and LED placed on a coin to show scale.

Temperature Measurement Module:

The cast saw embodiments, 1001, 1002, 1003 all comprise at least one temperature measurement instrument or module or data generating module, 100, 200, 300, which generates data correlative to the temperature of the cutting device, i.e., the saw blade. The data generated is in the form of an electrical signal, or optionally may be in the form of a radio wave if a wireless connection is contemplated. Non-limiting examples of temperature measurement instruments or modules or data generating modules 100, 200, 300 include thermistors, thermocouples, infrared detectors, a combination including one thermocouple and one infrared detector, or a combination including at least one thermocouple and at least one infrared detector. These devices may have the ability to convert an electrical signal to a wireless signal in the form of a radio wave, in an embodiment. These temperature measurement instruments 100, 200, 300 may be located in the shroud surrounding the cutting blade, or if there is no shroud, may be located on the cast saw, placed so as to be capable of measuring a temperature of the cutting blade, or an air or cast temperature in very close proximity to the cutting blade. It should be understood in the present disclosure that the term, "a (or the) temperature of a (or the) cutting blade" may in be a temperature of an area very near to, i.e., less than 1 mm away from the blade or less than 2 mm away from the blade or less than 3 mm away from the blade or less than 4 mm away from the blade or less than 5 mm away from the blade or less than 6 mm away from the blade or less than 7 mm away from the blade or less than 10 mm away from the blade or less than 15 mm away from the blade or less than 20 mm away from the blade or less than 25 mm away from the blade, but not touching the cutting blade. For example such an area may be the freshly cut surface of the cast. Such an area in close proximity to the blade may comprise air, or may comprise the cast material as it is being cut. A person having skill in the art can readily appreciate that it is difficult to measure a temperature of a rapidly moving object such as the oscillating cast saw cutting blade, and therefore the temperature of the air and/or the cast material in near proximity to the cutting blade is assumed to be related to the actual temperature of the cutting blade, i.e. if the air and/or cast very near or touching the cutting blade is hot, the cutting blade itself may assumed to be likewise hot since the friction of the cutting blade against the cast material creates heat, leading to temperature rise of the blade and the area surrounding and touching it, e.g. the freshly cut surface of the cast. Therefore, while the blade may not be exactly the same temperature as the air/and or cast material, their temperature, measured in very close proximity to the blade, may be measured as a proxy for the rapidly moving blade. FIG. 17 shows a photo of an embodiment of a temperature measurement module in the form of two infrared detectors 1702 with an associated printed circuit board 1706 to process the signal from the infrared detector.

Temperature Notification Module:

The cast saws 1001, 1002, 1003 each also comprise a temperature notification module 101, 201, 301 as shown in FIGS. 1, 2 and 3, respectively. The temperature notification module 101, 201, 301 serves to alert a user of the cast saw that the cutting blade, or the cast immediately next to the cutting blade, e.g. the fresh cut surface of the cast, is becoming too hot, preferably before a dangerous temperature is attained, meaning a temperature capable of burning the skin of the patient whose cast is being cut off. A non-limiting example of such temperature notification modules 101, 201, 301 are light emitting diode (LED) lights. Other non-limiting examples of temperature notifications are sounding an alarm, or an alphanumeric display. In particular, colored LED lights may be used, for instance a single LED that in response to an appropriate signal regarding the temperature of the blade (or area around it) from the data collection and processing module (i.e. computer) can turn from green to yellow to red. Also suitable are a plurality of differently colored LEDs that are sequentially or alternately energized (lit) in response to a signal corresponding to temperature from the data collection and processing module. For instance, if the blade is less than or equal to 35° C., the LED displays green or a green LED is energized. If the blade is hotter than 35° C. and cooler than 40° C., the LED displays yellow or a yellow LED is energized. If the blade is hotter than 40° C. the LED displays red, or a red LED is energized. For example one LED may light for temperatures less than or equal to 35° C., two LEDs may light up for temperatures hotter than 35° C. and cooler than 40° C., and three LEDs may light up for temperatures hotter than 40° C. Alternatively, other temperatures ranges may be selected as the safe ranges. Further, other temperatures ranges may be selected for the indicated zones or other visual displays may be employed to provide a more continuous display of temperature during operation. In this way, the practitioner is notified that the temperature is safe (green), or that the temperature is rising indication caution (yellow) or that the temperature is too hot (red). The practitioner may then turn off the saw and wait for the temperature notification module, i.e. the LED color, to alert them that the blade and/or the cast has returned to a safe temperature before turning the saw back on and continuing to cut through the cast. Alternatively, other temperatures ranges may be selected as the safe range, for instance, less than 37° C. or less than 36° C. or less than 34° C. or less than 33° C. or less than 32° C., or less than 30° C. or less than 25° C. with the ranges of the caution range accordingly adjusted to between 37° C. and 40° C., or between 36° C. and 40° C., or between 34° C. and 40° C., or between 33° C. and 40° C., or between 32° C. and 40° C., or between 30° C. and 40° C., or between 25° C. and 40° C. for instance. Another exemplary such range is green (safe) would represent 25° C. or less, yellow (caution) would represent the 35° C. to 45° C. range and the red light (too hot) would represent 45.5° C. or above. Similar temperature range indications may alternatively use multiple LED lights, as discussed above. FIG. 17 shows an embodiment of temperature indicator in the form of an LED 1704 that may be mounted in a cast saw is disclosed herein.

Data Collection and Processing Module:

The cast saws 1001, 1002, 1003 each also comprise a data collection and processing module 103, 203, 303, respectively in the form of a computer, which may be internal or external to the saw and if external, may be connected via a wireless connection (e.g. BLUETOOTH® or another wireless networking technology that may use radio waves to provide wireless high-speed Internet and/or network connections, e.g. Wi-Fi™ IEEE 802.11x) or a wired connection, such as an electrical cord attached with universal serial bus (USB) connections of any suitable type, or simply be hard-wired. The dashed lines 105, 205, 305 in each of FIGS. 1, 2, and 3, respectively represent the wired and/or wireless communication from the cast saws 1001, 1002, 1003 to the data collection and processing module 103, 203, 303.

The type of computer is not particularly limited and may be a personal computer such as a laptop or a desktop computer or a tablet, or may be a smartphone or a wrist unit, all such as are known and used in the art. The computer may also be a controller or processor, e.g. a microcontroller unit or a microprocessor unit or a system on a chip located on a printed circuit board (PCB) and may be located in an external device or may be on-board the cast saw, for example in a handle of an embodiment of a cast saw.

The purpose of the computer (i.e. the data collection and processing module) in the cast saw is to first collect the data in the form of an electrical signal or radio wave (if a wireless connection is used) produced by the data generating module, i.e. the temperature measuring device such as a thermocouple or an infrared detector in response to the temperature. The computer then converts the temperature data from the infrared detector or thermocouple, and converts it to a signal which is received by the LED or LEDs (i.e. the temperature notification module). The LED or LEDs then produce a temperature output in the form of a colored light or lights, as described above. The practitioner cutting the cast will then observe the lights and take appropriate action depending on the color of the light or lights or how many of the lights are energized, for instance.

Figure 4:
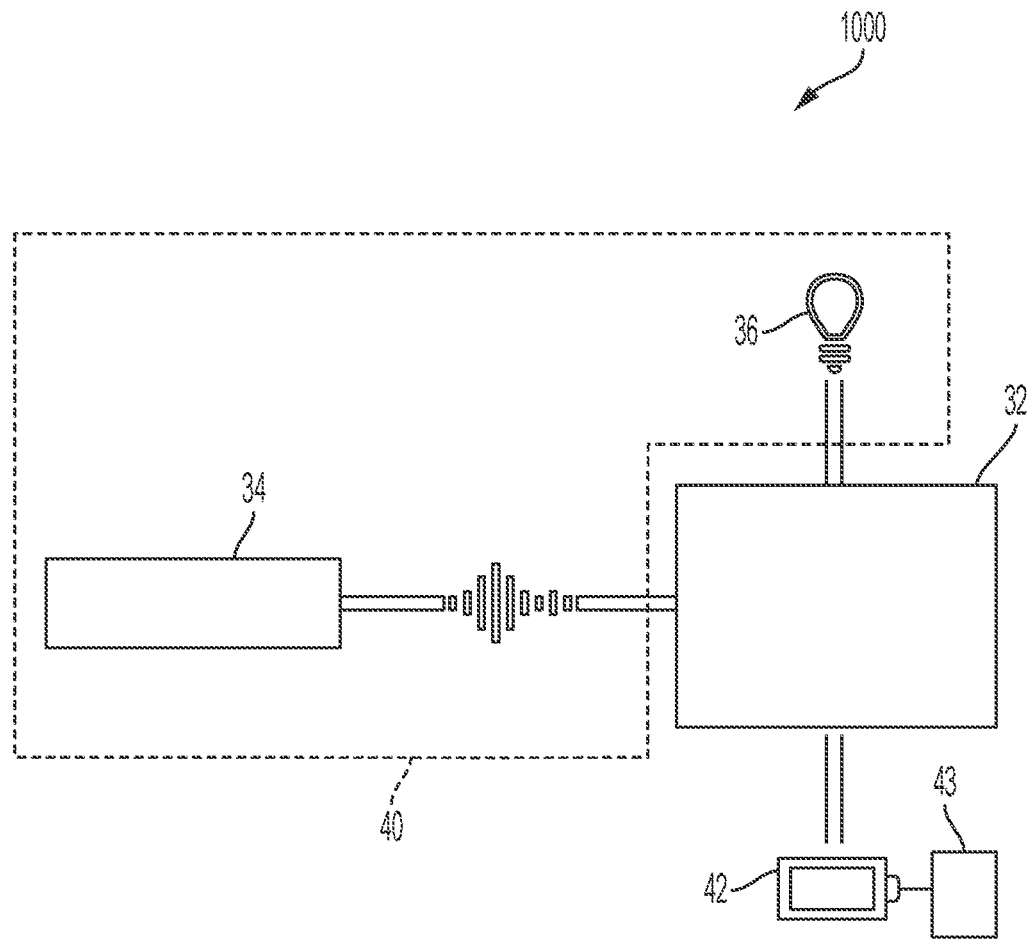
FIG. 4 shows a schematic of an embodiment of the electrical aspects of a cast saw.

FIG. 4 shows a schematic representation of the interconnectivity of a data collection and processing module 32 such as a computer with a data generating module 34 such as an infrared sensor or a thermocouple and a temperature notification module 36 such as an LED or a plurality of LEDs. As can be seen in FIG. 4, the data generating module (e.g. infrared sensor or a thermocouple) 34 and the temperature notification module (e.g. LED) 36 are contained within a power tool (e.g. cast saw) 1000 and preferably are contained within a shroud 40 surrounding a blade (not shown). The shroud 40 is shown schematically in FIG. 4 as the area surrounded by the dashed line. The computer (i.e. data collection and processing module 32) as well as a power supply 42 for the cast saw 1000 as well as the computer 32, the infrared detector or thermocouple 34 and the LED light(s) may be external to the cast saw 1000, but both or either may be included on-board the cast saw 1000, in alternative embodiments. Optionally, the power tool or cast saw 1000 may include a power supply status and display module 43. The power supply status and display module 43 may, for example comprise a voltage measuring device associated with the power supply that provides a notification, such a light, to indicate that the power supply 42 is low.

Figure 5:
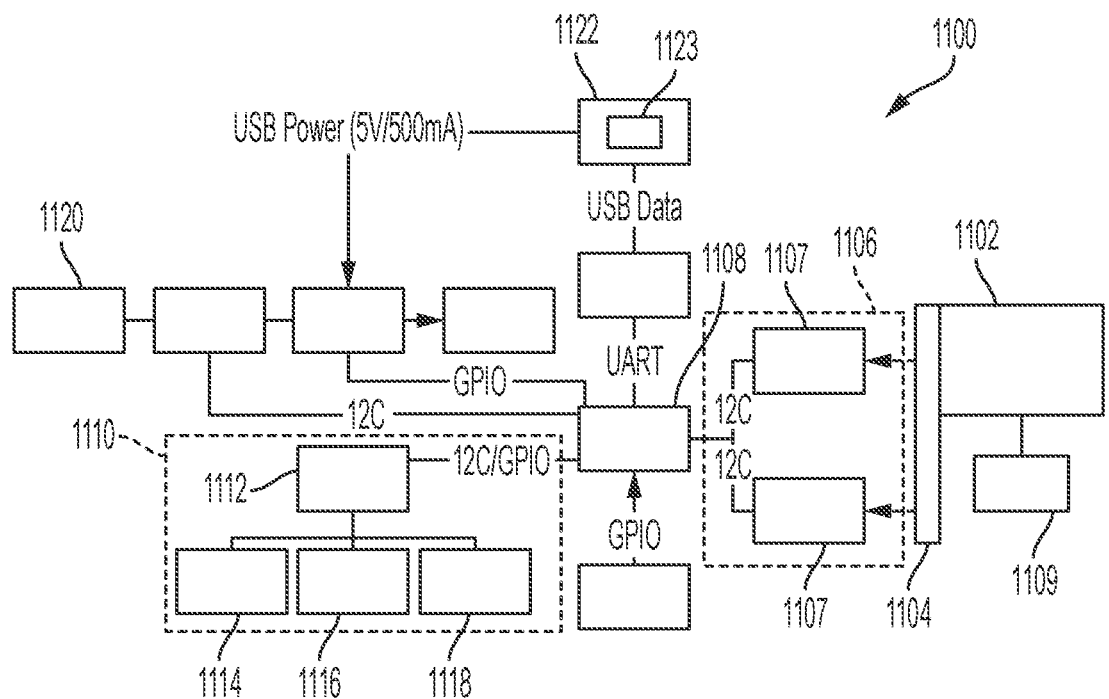
FIG. 5 shows a schematic of another embodiment of the electrical aspects of a cast saw.

FIG. 5 shows a more detailed block diagram of another embodiment of the power tool or cast saw 1100. Block 1102 represents a body, e.g. a handle 1102 of the cast saw 1100 and block 1104 represents the cutting device (blade) of the cast saw 1100. As seen in the diagram in FIG. 5, a data generating module 1106 which comprises infrared detector(s) and/or thermocouple(s) 1107, generates data from the blade 1104 or an area very near the blade, as described above, which is correlative to the temperature of the blade. A data collection and processing module 1108 collects the data correlative to the temperature of the cutting device 1104 from the data generating module 1106, and processes the data to determine the temperature of the cutting device 1104. The cast saw 1100 may have an ON/OFF switch 1109. The data collection and processing module 1108 is connected, to the temperature notification module 1110 which in this example comprises an LED driver 1112 connected to three differently colored LED lights 1114, 1116, 1118, which may be respectively red, yellow and green, for instance. As shown in this exemplary embodiment, the data collection and processing module (computer) 1108, the data generating module 1106 (infrared detector(s) and/or thermocouple(s)) and the temperature notification module 1110 (LED's 1114, 1116, 1118 and associated driver 1112) are powered by a rechargeable battery 1120. The battery 1120 may be charged via an external power source 1122, which may also provide power to the data collection and processing module (computer) 1108, the data generating module 1106 (infrared detector(s) and/or thermocouple(s)) and the temperature notification module 1110. Although not shown, the cast saw 1102 may also be powered by the battery 1120 or the external power source 1122, or by a separate battery and/or external power source. The external power source 1122 may have associated with it a power supply status and display module 1123 capable of detecting and displaying the charge status of the battery 1120.

The shroud 40, as seen in FIG. 1 as part 28 and in FIG. 2 as part 30 may have a variety of configurations, depending on the number of infrared sensors or thermocouples utilized as the data generating module and depending on the number of LEDs utilized as the temperature notification module. Accordingly, the following detailed description shows a variety of embodiments of shrouds (28 or 30) surrounding the cutting blade (parts 10 or 12 in FIGS. 1 and 2) of a power tool, i.e. a cast saw (1001 or 1002 in FIG. 1 or 2) that may be utilized to house the infrared sensor or thermocouple and the LED light or lights.

Figure 6:
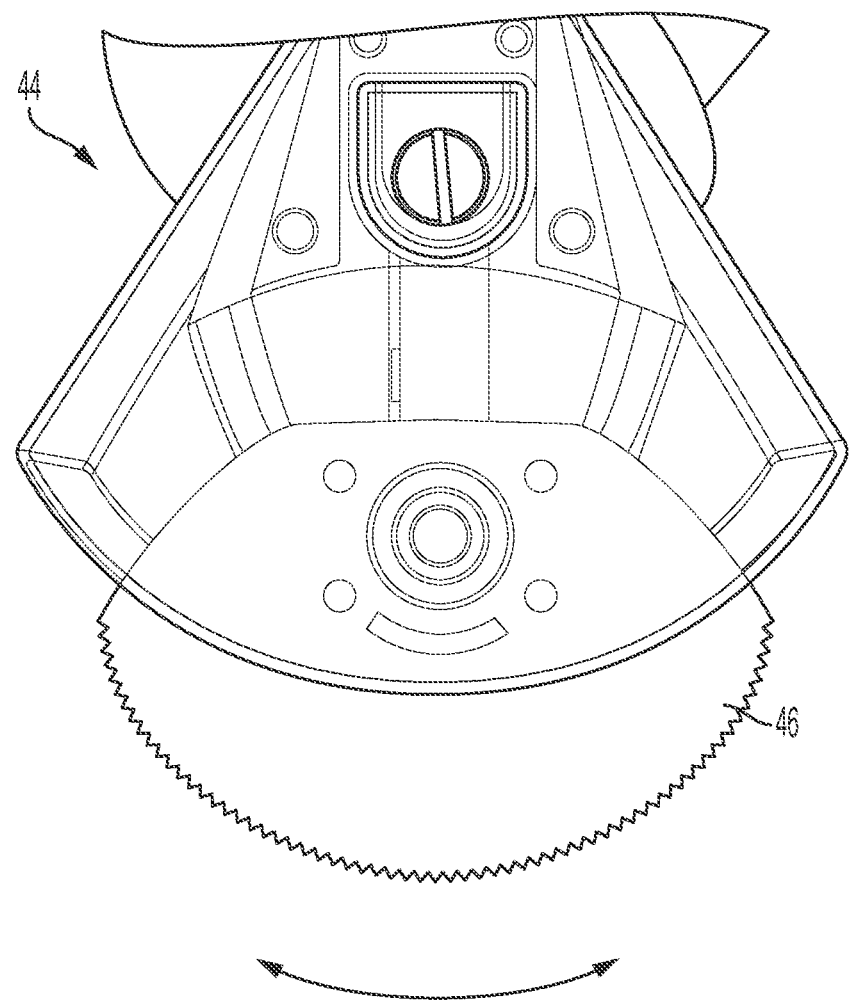
FIG. 6 shows a shroud installed on a cast saw.

FIG. 6 shows a front side view, parallel to the handle of a shroud 44 mounted over and partially surrounding a cutting blade 46. The double sided arrow in FIG. 5 shows the direction of oscillation of the blade 46 during operation of the cast saw.

Figure 7:
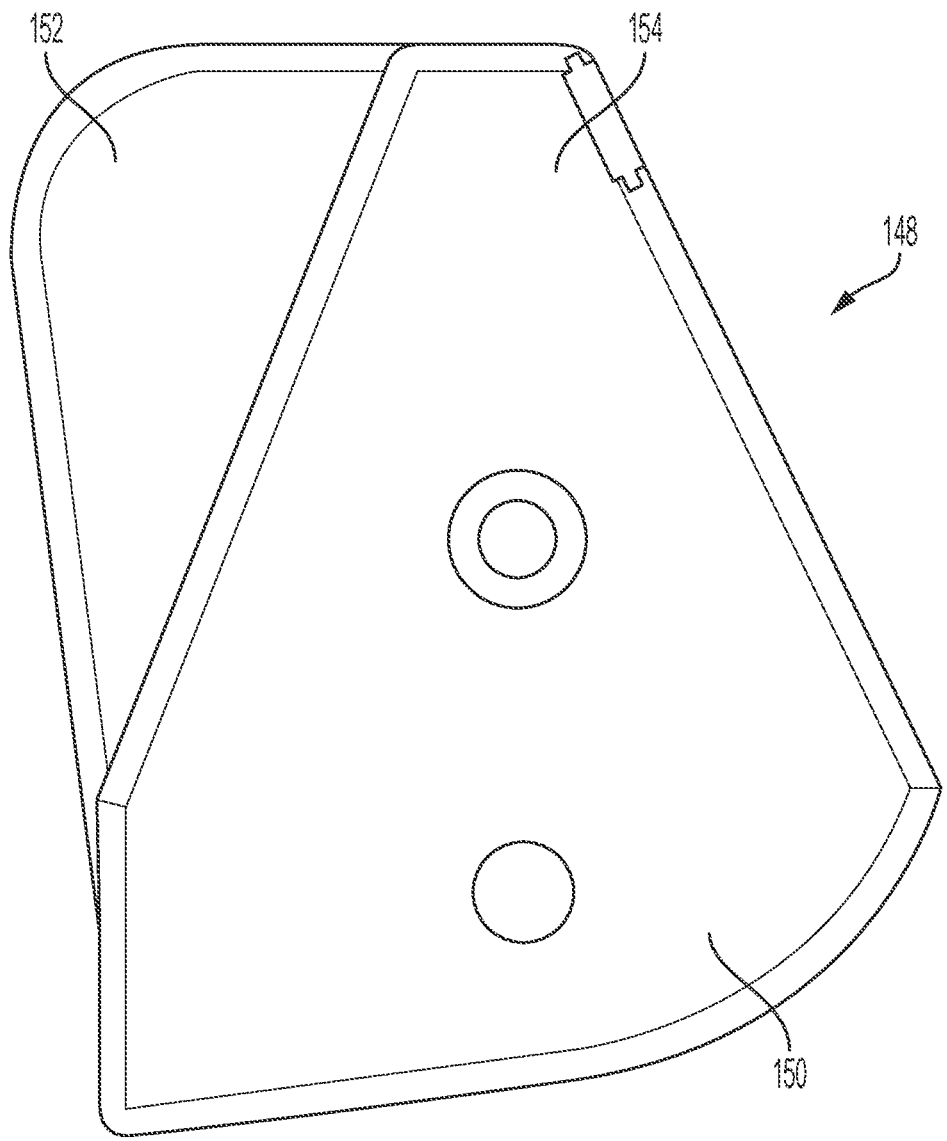
FIG. 7 shows a first embodiment of a shroud according to the present disclosure.

Turning next to FIG. 7, which likewise shows a front side view, parallel to the handle of a first embodiment shroud 148. The shroud 148 comprises a first housing portion 150 which is configured to at least partially enclose the cutting blade (not shown) for the cast saw (not shown). The shroud 148 also comprises a second housing portion 152, which is configured to hold at least one infrared detector (not shown) or thermocouple (not shown) so that the detecting end of either the infrared detector or the thermocouple is fixedly held in close, but not touching proximity to the cutting blade. The detector or thermocouple should be within at least 10 mm of the blade or within at least 9 mm of the blade or within at least 8 mm of the blade or within at least 7 mm of the blade or within at least 6 mm of the blade or within at least 5 mm of the blade or within at least 4 mm of the blade or within at least 3 mm of the blade or within at least 2 mm of the blade or within at least 1 mm of the blade. Alternatively, since as discussed above, it is understood that the freshly cut portion of the cast also may become hot during the cutting operation, the detector may be held in place by the second housing portion 152 of the shroud 148 in close or even touching proximity to the freshly cut portion of the cast. It is possible for the detector to touch the freshly cut cast, since unlike the blade, the cast is not oscillating. As with the blade, in order to collect accurate data, the detector should be with 3 mm or 2 mm or 1 mm of (if not touching) the freshly cut surface of the cast. Also shown in FIG. 7 is a third housing portion 154. This third housing portion is constructed and arranged to hold the temperature notification module (not shown), i.e. one or more LED lights that function to alert the medical practitioner regarding the temperature of the blade and/or the freshly cut surface of the cast.

Figure 8:
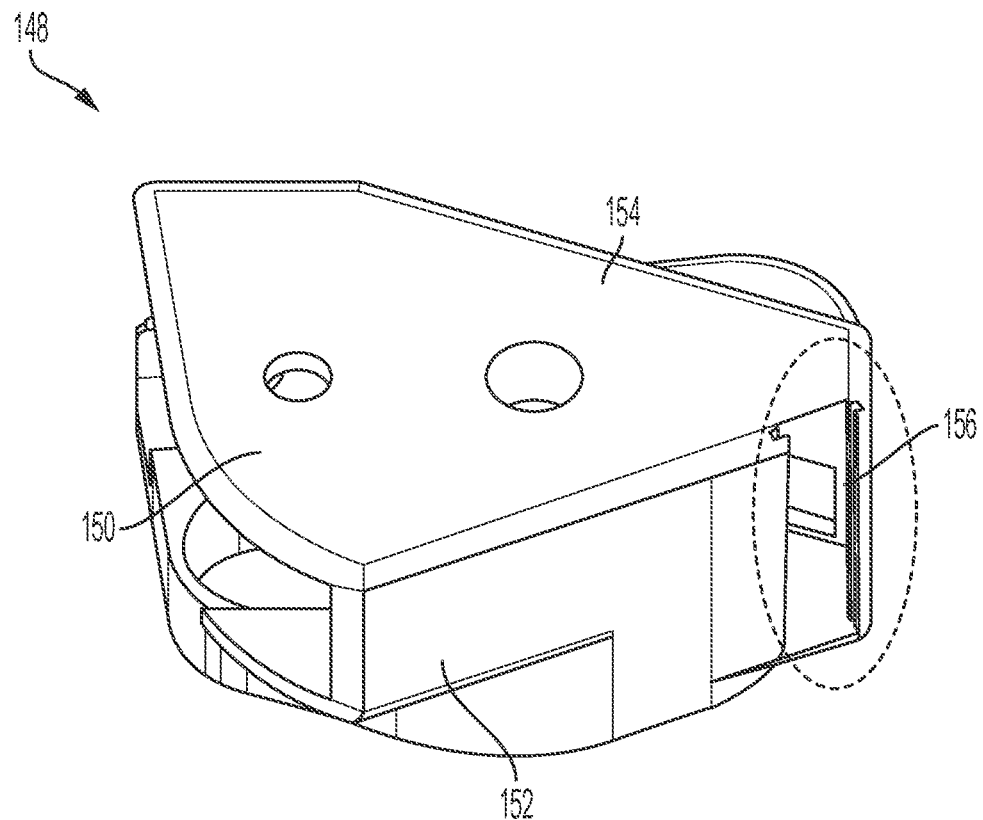
FIG. 8 shows another view of the shroud shown in FIG. 7.
Figure 9:
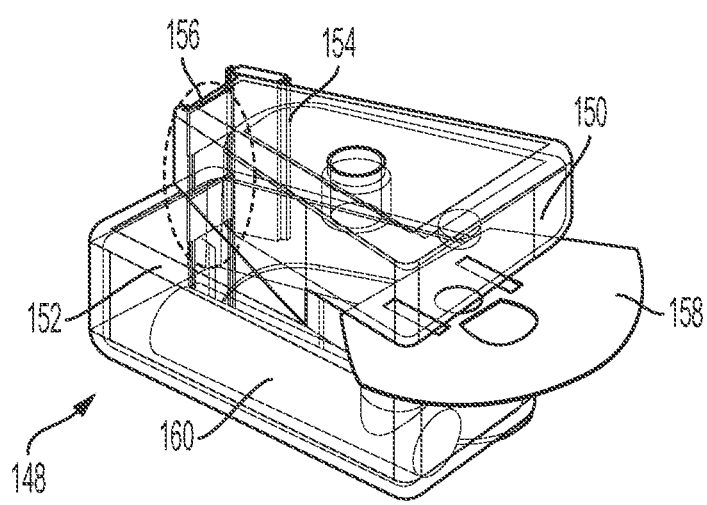
FIG. 9 shows another view of the shroud shown in FIG. 7.

FIG. 8 shows a side isometric view of the first embodiment shroud 148. In this view, in addition to the first housing portion 150, the second housing portion 152 and the third housing portion 154, also visible is an aperture 156 which is part of the second housing portion 152. This aperture 156 is constructed and arranged to permit a temperature notification module to be installed therein. For instance if the temperature notification module comprises one or more LED's they may be visible to an operator (medical practitioner) via the aperture 156. FIG. 9 shows a transparent rendering of the first embodiment shroud 148. In this view a blade 158 is shown in place in the first housing portion 150. Also shown schematically in this rendering is a data generating module 160 (e.g. an infrared detector) in place in the second housing portion 152.

Figure 10:
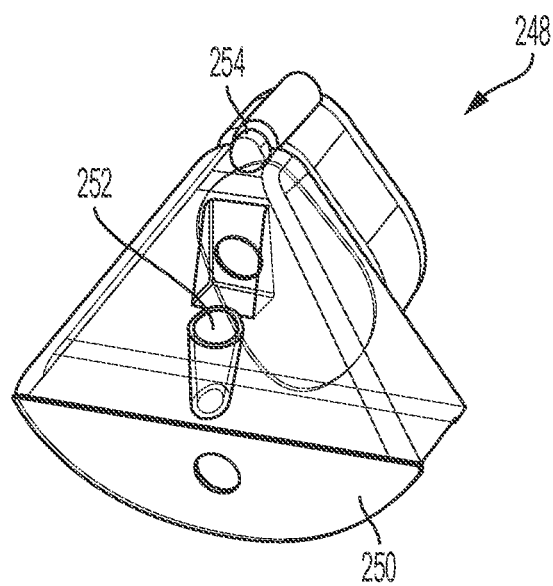
FIG. 10 shows a second embodiment of a shroud according to the present disclosure.

FIG. 10 shows an isometric view of a second embodiment of the shroud 248 for the cutting blade of a power tool. This second embodiment shroud 248 comprises again a generally arcuate first housing portion 250 for the cutting blade (not shown). As can be seen in FIG. 8, this embodiment 248 also comprises a second housing portion 252 that is constructed and arranged to hold a single infrared or thermocouple (not shown) in non-contacting proximity to the cutting blade (not shown), or alternatively or additionally in contact or close proximity to the freshly cut cast. Note that in FIG. 10, the second housing portion 252 is formed as a cylindrical opening into which an infrared detector or thermocouple may be inserted. The size of the cylindrical opening may be adjusted as necessary, depending on the size of the infrared detector or thermocouple that is intended to be inserted therein.

Figure 12:
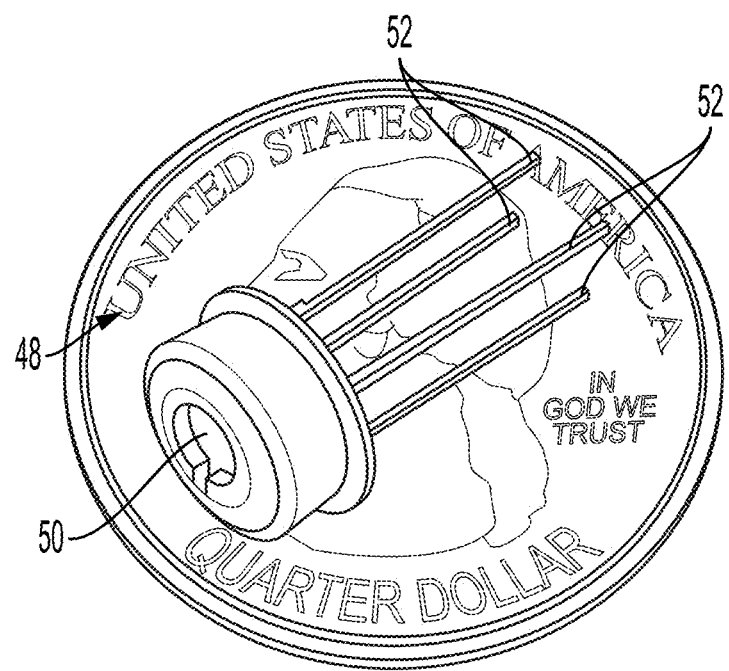
FIG. 12 is a photograph view of an exemplary infrared detector placed on a coin to show scale.
Figure 13:
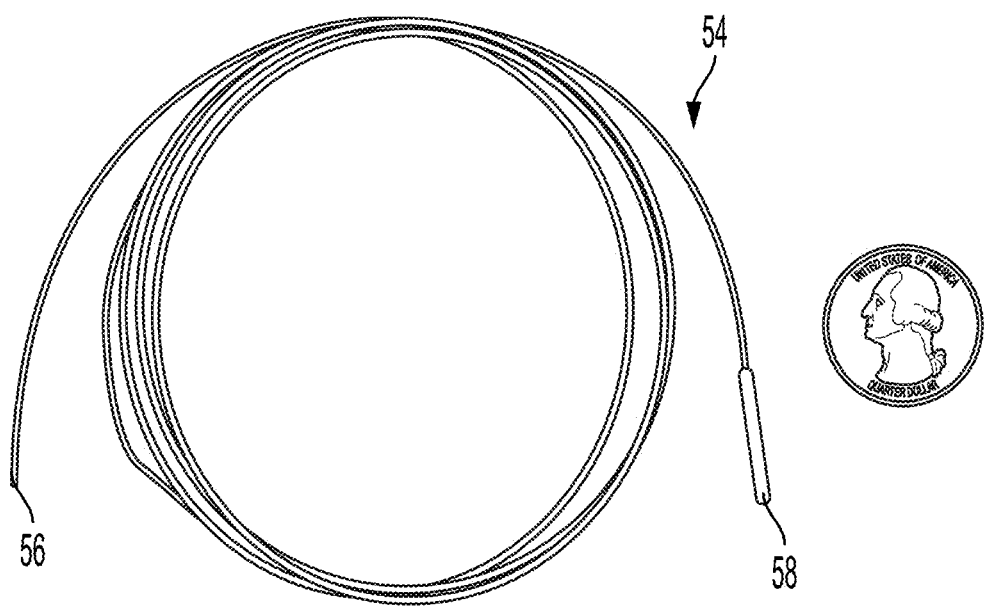
FIG. 13 is a photograph of an exemplary thermocouple placed next to a coin to show scale.

Turning briefly to FIG. 12, which shows a photograph of a non-limiting example of an infrared detector 48. The detector (or window) end 50 of the infrared detector 48 is inserted into the second housing portion 252 of the second embodiment shroud 248, with wires 52 thus emerging upwards in the orientation shown in FIG. 10, out of the second housing portion 252. These wires 52 are connected as appropriate to the computer and power source (neither shown). FIG. 13 shows an exemplary thermocouple 54. Any suitable ASTM type thermocouple may be utilized and ASTM type K is exemplary. The measurement junction end 56 of the thermocouple 54 is inserted into the second housing portion 252 of the second embodiment shroud 248, with connection end 58 thus emerging upwards in the orientation shown in FIG. 10, out of the second housing portion 252. The connection end 58 is connected as appropriate to the computer (neither shown).

Figures 11A, 11B:
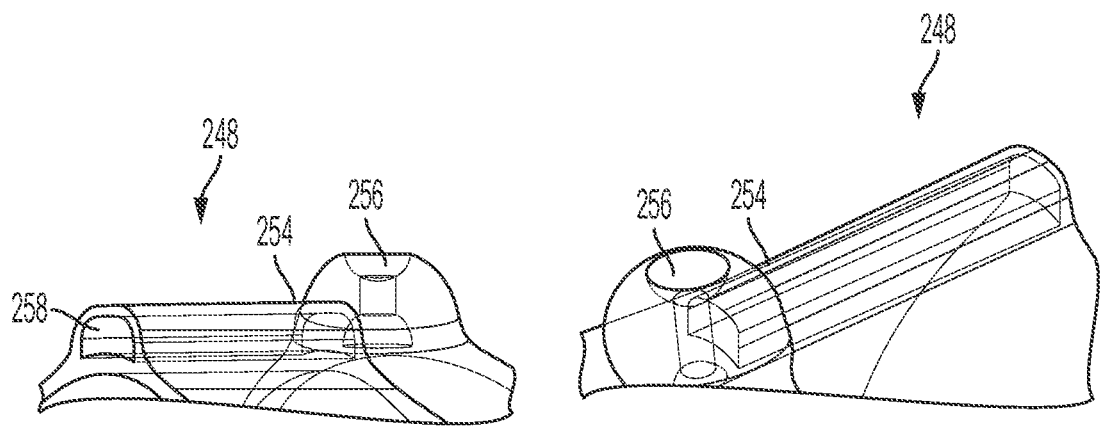
FIGS. 11A and 11B show two views of an element of the shroud shown in FIG. 10.

Also shown in FIG. 10 is a third housing portion 254 for the temperature notification module, which in this embodiment is a single LED (not shown) that is able to produce different colors in response to a signal from a computer, i.e. the data collection and processing module (not shown). FIGS. 11A and 11B show two different views of the third housing portion 254 which is constructed and arranged to hold the single LED, which is not shown. As seen in FIGS. 11A and 11B, the third housing portion 254 in this second embodiment shroud 248 has a first opening 256 for the lighted portion of the LED and a second opening 258 in communication with the first opening 256 and oriented approximately perpendicular to the first opening 256. This second opening 258 is intended for wires that supply power to the LED from a power source as well the temperature of the cutting blade and/or an area of the cast from the data collection and processing module (computer). When the shroud 248 is installed on the cast saw and the cast saw is in operation, the LED will face generally away from the cast being cut and towards the practitioner cutting the cast, so that the color of the LED is readily visible to the practitioner.

Figure 14:
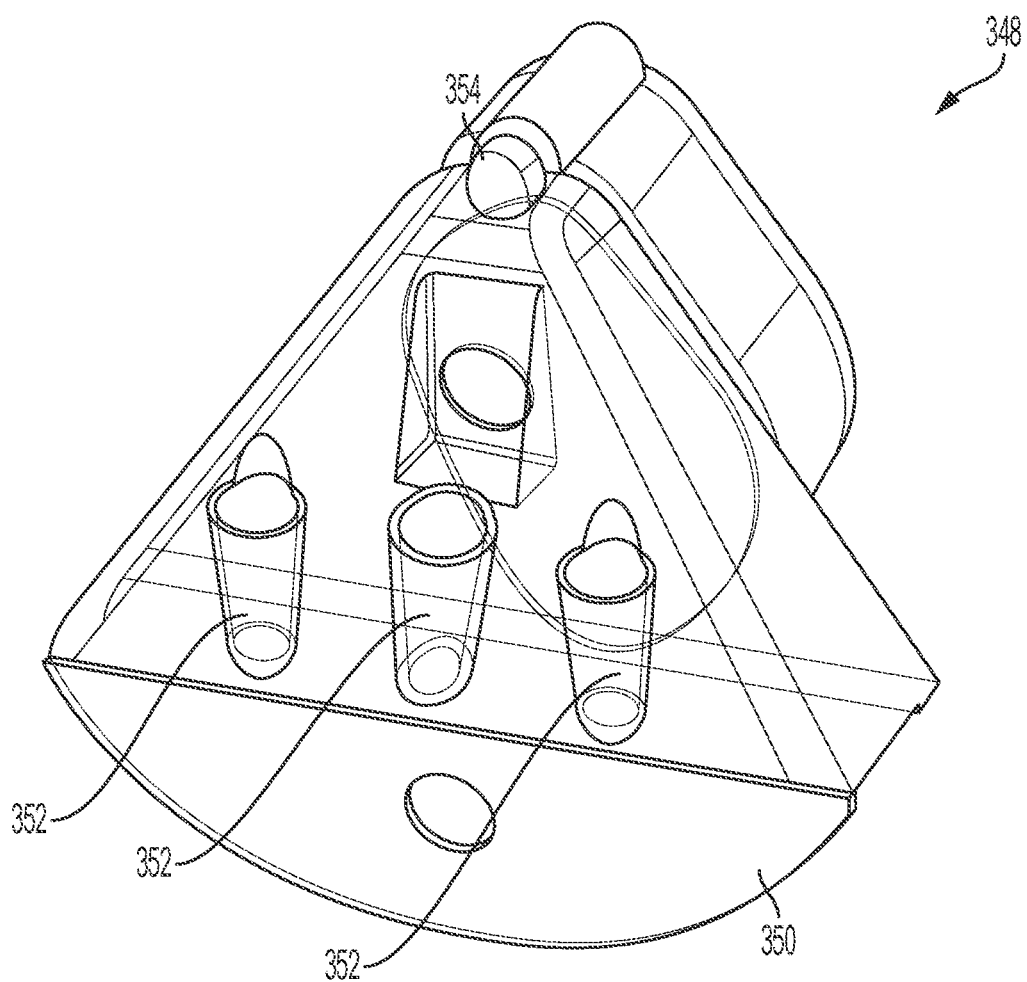
FIG. 14 is a view of a third embodiment of a shroud according to the present disclosure.

FIG. 14 shows an isometric view of a third embodiment of a shroud 348 for the cutting blade of a cast saw (not shown). The shroud 348 comprises a generally arcuate first housing portion 350 for the cutting blade (not shown). As can be seen in FIG. 11, this embodiment 348 also comprises a second housing portion 352 that is constructed and arranged to hold three infrared detectors or thermocouples (not shown) in non-contacting proximity to the cutting blade (not shown), or alternatively or additionally in contact or close proximity to the freshly cut cast. Note that in FIG. 14, the second housing portion 352 is formed as three cylindrical openings into each of which an infrared detector or thermocouple may be inserted. The size of the cylindrical openings may be adjusted as necessary, depending on the size of the infrared detectors or thermocouples that are intended to be inserted therein. Also shown in FIG. 14 is a third housing portion 254 for the temperature notification module, which in this embodiment is a single LED (not shown) that is able to produce different colors in response to a signal from a computer, i.e. the data collection and processing module (not shown).

Exemplary aspects of the present disclosure are as follows:

Aspect 1: A power tool operable by a user, the power tool comprising:
  a) a cutting device having a temperature;
  b) a data generating module, which is configured to generate data correlative to the temperature of the cutting device;
  c) a data collection and processing module which is configured to: i) collect the data correlative to the temperature of the cutting device, and ii) process the data correlative to the temperature of the cutting device to determine the temperature of the cutting device;
  d) a temperature notification module which is configured to: i) receive the temperature of the cutting device from the data collection and processing module, and ii) produce a temperature output that can be detected by the user.

Aspect 2: The power tool operable by a user according to Aspect 1, wherein the cutting device comprises a metal blade.

Aspect 3: The power tool operable by a user according to either of Aspects 1 and 2, wherein the data generating module comprises at least one of an infrared sensor and a thermocouple.

Aspect 4: The power tool operable by a user according to any of Aspects 1-3, wherein the data collection and processing module comprises a computer.

Aspect 5: The power tool operable by a user according to any of Aspects 1-4, wherein the temperature notification module comprises at least one light emitting diode (LED).

Aspect 6: The power tool operable by a user according to any of Aspects 1-5, wherein the at least one LED corresponds to a temperature range.

Aspect 7: The power tool operable by a user according to any of Aspects 1-6, wherein the temperature notification module is configured to illuminate the at least one LED in response to the temperature of the cutting device from the data collection and processing module.

Aspect 8: The power tool operable by a user according to any of Aspects 1-7, wherein the power tool comprises a cast saw.

Aspect 9: The power tool operable by a user according to any of Aspects 1-8, wherein the cutting device comprises a metal blade and a shroud at least partly surrounding the metal blade.

Aspect 10: The power tool operable by a user according to any of Aspects 1-9, wherein the shroud surrounding the metal blade houses the data generating module.

Aspect 11: The power tool operable by a user according to any of Aspects 1-10, wherein the data generating module comprises at least one of an infrared detector and a thermocouple.

Aspect 12: The power tool operable by a user according to any of Aspects 1-11, wherein the shroud surrounding the metal blade houses the temperature notification module.

Aspect 13: The power tool operable by a user according to any of Aspects 1-12, wherein the temperature notification module comprises at least one light emitting diode (LED) and wherein a color of the at least one LED corresponds to a temperature range.

Aspect 14: The power tool operable by a user according to any of Aspects 1-13, wherein the temperature notification module comprises a first LED, a second LED, and a third LED, and wherein the first LED is turned ON when the temperature of the cutting device from the data collection and processing module is within a first temperature range, the second LED is turned ON when the temperature of the cutting device from the data collection and processing module is within a second temperature range, and the third LED is turned ON when the temperature of the cutting device from the data collection and processing module range is within a third temperature range.

Aspect 15: The power tool operable by a user according to any of Aspects 1-14, wherein the first temperature range is lower than the second temperature range and the third temperature range, and the second temperature range is lower than the third temperature range.

Aspect 16: A shroud for a cutting blade of a power tool, the shroud comprising,
  a first housing portion for the cutting blade;
  a second housing portion for a data generating module configured to generate data correlative to a temperature of the cutting blade; and
  a third housing portion for a temperature notification module configured to produce a temperature output that can be sensed by a user of the power tool.

Aspect 17: The shroud for a cutting blade of a power tool according to Aspect 16, further comprising a data generating module, wherein the data generating module comprises at least one of an infrared detector or a thermocouple.

Aspect 18: The shroud for a cutting blade of a power tool according to either of Aspects 16 or 17, wherein the third housing portion is configured to hold the at least one of the infrared detector or the thermocouple within non-contacting proximity to and no more than 3 mm away from the cutting blade.

Aspect 19: The shroud for a cutting blade of a power tool according to any of Aspects 16-18, wherein the third housing portion is configured to hold the at least one of the infrared detector or the thermocouple within non-contacting proximity to and no more than 2 mm away from the cutting blade.

Aspect 20: The shroud for a cutting blade of a power tool according to any of Aspects 16-19, wherein the third housing portion is configured to hold the at least one of the infrared detector or the thermocouple within non-contacting proximity to and no more than 1 mm away from the cutting blade.

Aspect 21: A method of operating a cast saw to cut a cast off of a patient, the method comprising the steps of:
 1) providing a cast saw wherein the cast saw comprises:
  a) a cutting device having a temperature;
  b) a data generating module configured to generate data correlative to the temperature of the cutting device;
  c) a data collection and processing module which is configured to: i) collect the data correlative to the temperature of the cutting device, and ii) process the data correlative to the temperature of the cutting device to determine the temperature of the cutting device;
  d) a temperature notification module which is configured to: i) receive the temperature of the cutting device from the data collection and processing module, ii) produce a first temperature output corresponding to a safe temperature of the cutting device, and iii) produce a second temperature output corresponding to an excessive temperature of the cutting device, wherein the first output and the second output can be detected by a user of the cast saw;
  e) an ON/OFF switch;
 2) detecting that the temperature notification module is producing the first temperature output and is not producing the second temperature output;
 3) turning the ON/OFF switch to ON and operating the cast saw to cut the cast;
 4) turning the ON/OFF switch to OFF when the cast is completely cut.

Aspect 22: The method according to Aspect 21, further comprising the step of:
 3a) turning the ON/OFF switch to OFF when detecting that the temperature notification module is producing the second temperature output.

Aspect 23: The method according to either of Aspects 21 or 22, further comprising the step of repeating steps 3) and 3a) until the cast is completely cut.

Aspect 24: The method according to any of Aspects 21-23, wherein the temperature notification module is further configured to: iii) produce a third temperature output corresponding to a temperature of the cutting device higher than the safe temperature of the cutting device and lower than the excessive temperature of the cutting device.

Aspect 25: The method according to any of Aspects 21-24, further comprising the step of turning the ON/OFF switch to OFF when detecting that the temperature notification module is producing the third temperature output.

Aspect 26: The method according to any of Aspects 21-25, wherein the temperature notification module comprises at least one light emitting diode (LED) operable to produce a first color in response to the first temperature output, and a second color in response to the second temperature output.

Aspect 27: The method according to any of Aspects 21-26, wherein the temperature notification module comprises a first light emitting diode (LED) operable to produce a first color in response to the first temperature output, a second LED operable to produce a second color in response to the second temperature output, and a third LED operable to produce a third color in response to the third temperature output.

Aspect 28: The method according to any of Aspects 21-27, further comprising the step of turning the ON/OFF switch to OFF when detecting that the temperature notification module is producing the second temperature output or the third temperature output.

EXAMPLES

Figure 15:
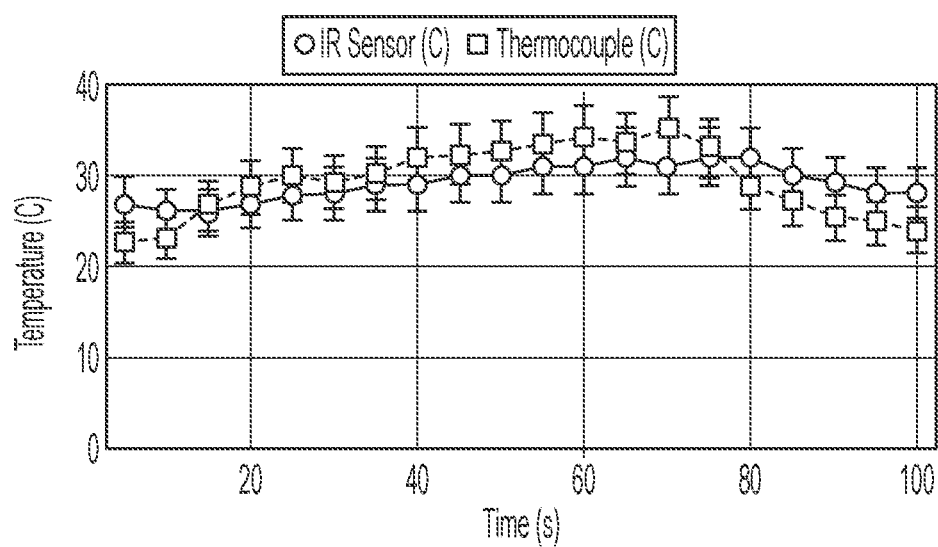
FIG. 15 is a plot of the temperature of the blade of a cast saw during a cutting operation.

Example 1: Cast Saw Blade Temperature Measurement During Cutting with Infrared Detector and Thermocouple The shroud shown in FIG. 8, with an integrated infrared sensor was installed on a cast saw and used to cut a fiberglass cast. A similar shroud utilizing a type K thermocouple in place of the infrared detector was also used to measure the temperature of the blade during a cutting operation. The temperature data vs. time is shown in FIG. 15 for both types of detectors. The data illustrates that the infrared detector and the thermocouple are both able to measure the temperature of a cast saw blade or the area very near to the blade while cutting a cast.

Further testing demonstrated that the temperature were measured accurately over the entire range from ambient room temperature 20° C. up to about 125° C.

Example 2: Practitioner Testing of Cast Saws

Three experienced medical practitioners utilized a cast saw equipped with a shroud similar to that shown in FIG. 14, using three infrared detectors and an LED capable of producing red, yellow or green light depending on the temperature ranges shown in Table 1 to cut real casts (not on patients, however). Feedback was provided as visual feedback using lights of different color to denote different temperature ranges. The purpose of the testing was to test accuracy, ergonomics and effectiveness of temperature notification using the LED. The practitioners operated the saw in a way that reflected normal use.

TABLE 1

Example 2 LED colors and temperature ranges

| Temperature Range | LED Color | Color Meaning |
| --- | --- | --- |
| <33° C. | Green | Safe |
| 35° C.-40° C. | Yellow | Caution |
| >40° C. | Red | Danger |

The test was conducted in two parts. The first part was intended to assess how much poor technique could affect the temperature of the blade (or the temperature of the area of the cast immediately surrounding the blade during cutting.) The three practitioners utilized the saw using both a proper technique, which in their experience does not lead to burns on patients and in a manner that they thought would likely lead to burns, i.e. an improper technique. The temperature of the saw blades during both techniques (proper and improper technique) during the cutting operation was measured. The results are shown in Table 2.

TABLE 2

Example 2 Proper vs. Improper Cutting Technique

| Practitioner | Proper Technique, Maximum Temperature, ° C. | Improper Technique, Maximum Temperature, ° C. |
| --- | --- | --- |
| Dr. A | 33 | 71 |
| Dr. B | 38 | 43 |
| Dr. C | 38 | 40 |

As shown in Table 2, the cutting technique can lead to significant temperature rise of the blade during the cutting operation.

The second part of the test was intended to assess the accuracy of the practitioner's assumption regarding how hot the blade was, compared to the actual temperature of the blade. This was done by utilizing the shroud comprising the infrared sensor, but covering up the LED light, so that the practitioner couldn't see it. The actual blade temperature was also measured, via a separate feed from the infrared detector. Two of the practitioners (Dr. A and Dr. B) made a number of cuts of the cast and attempted to guess what color the LED would read. The results of their guesses regarding LED color, the actual temperatures and the actual LED colors for this example are shown in Table 3 for Dr. A and in Table 4, for Dr. B.

TABLE 3

Example 2 Dr. A Blind Temperature Test

| Actual Temperature, ° C. | Guess Regarding LED color | Actual LED Color |
| --- | --- | --- |
| 29 | Green | Green |
| 33 | Yellow | Green |
| 29 | Green | Green |
| 35 | Yellow | Yellow |
| 30 | Green | Green |

TABLE 4

Example 2 Dr. B Blind Temperature Test

| Actual Temperature, ° C. | Guess Regarding LED color | Actual LED Color |
| --- | --- | --- |
| 30 | Green | Green |
| 41 | Yellow | Red |
| 29 | Green | Green |
| 34 | Yellow | Yellow |
| 30 | Green | Green |
| 32 | Yellow | Green |

Notably, both experienced practitioners were more likely to err on the side of caution, i.e. to assume the blade was hotter than it was. However, out of 11 total tests, in one instance, even an experienced and cautious practitioner underestimated the temperature range of the blade during the cutting operation, thereby demonstrating that the cast saw and its temperature measurement disclosed herein accurately determines whether a patient may be burned during a cast cutting operation and is capable of preventing a burn injury.

In addition, it was observed in further testing that the practitioners changed their cutting technique due to the feedback provided by the temperature monitoring device. For example, practitioners took more frequent but shorter pauses between cuts to allow the blade to stay cool.

Within this specification embodiments have been described in a way which enables a clear and concise specification to be written, but it in intended and will be appreciated that embodiments may be variously combined or separated without departing from the invention. For example, it will be appreciated that all preferred features described herein are applicable to all aspects of the invention described herein.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A power tool operable by a user, the power tool comprising:
    a) a cutting device having a temperature;
    b) a data generating module, which is configured to generate data correlative to the temperature of the cutting device;
    c) a data collection and processing module which is configured to:
        i) collect the data correlative to the temperature of the cutting device, and
        ii) process the data correlative to the temperature of the cutting device to determine the temperature of the cutting device;
    d) a temperature notification module which is configured to:
        i) receive the temperature of the cutting device from the data collection and processing module, and
        ii) produce a temperature output that can be detected by the user,
        wherein the temperature notification module comprises a first LED, a second LED, and a third LED, and wherein the first LED is turned ON when the temperature of the cutting device from the data collection and processing module is within a first temperature range, the second LED is turned ON when the temperature of the cutting device from the data collection and processing module is within a second temperature range, and the third LED is turned ON when the temperature of the cutting device from the data collection and processing module range is within a third temperature range.

2. The power tool operable by a user according to claim 1, wherein the cutting device comprises a metal blade.

3. The power tool operable by a user according to claim 1, wherein the data generating module comprises at least one of an infrared sensor and a thermocouple.

4. The power tool operable by a user according to claim 1, wherein the data collection and processing module comprises a computer.

5. The power tool operable by a user according to claim 1, wherein the temperature notification module comprises at least one light emitting diode (LED).

6. The power tool operable by a user according to claim 5, wherein the at least one LED corresponds to a temperature range.

7. The power tool operable by a user according to claim 5, wherein the temperature notification module is configured to illuminate the at least one LED in response to the temperature of the cutting device from the data collection and processing module.

8. The power tool operable by a user according to claim 1, wherein the power tool comprises a cast saw.

9. A power tool operable by a user, the power tool comprising:
   a) a cutting device having a temperature, wherein the cutting device comprises a metal blade and a shroud at least partly surrounding the metal blade;
   b) a data generating module, which is configured to generate data correlative to the temperature of the cutting device;
   c) a data collection and processing module which is configured to:
      i) collect the data correlative to the temperature of the cutting device, and
      ii) process the data correlative to the temperature of the cutting device to determine the temperature of the cutting device;
   d) a temperature notification module which is configured to:
      i) receive the temperature of the cutting device from the data collection and processing module, and
      ii) produce a temperature output that can be detected by the user.

10. The power tool operable by a user according to claim 9, wherein the shroud surrounding the metal blade houses the data generating module.

11. The power tool operable by a user according to claim 10, wherein the data generating module comprises at least one of an infrared detector and a thermocouple.

12. The power tool operable by a user according to claim 9, wherein the shroud surrounding the metal blade houses the temperature notification module.

13. The power tool operable by a user according to claim 9, wherein the temperature notification module comprises at least one light emitting diode (LED) and wherein a color of the at least one LED corresponds to a temperature range.

14. The power tool operable by a user according to claim 1, wherein the first temperature range is lower than the second temperature range and the third temperature range, and the second temperature range is lower than the third temperature range.

15. A shroud for a cutting blade of a power tool, the shroud comprising,
   a first housing portion for the cutting blade;
   a second housing portion for a data generating module configured to generate data correlative to a temperature of the cutting blade;
   a third housing portion for a temperature notification module configured to produce a temperature output that can be sensed by a user of the power tool; and
   a data generating module, wherein the data generating module comprises at least one of an infrared detector or a thermocouple,
   wherein the third housing portion is configured to hold the at least one of the infrared detector or the thermocouple within non-contacting proximity to and no more than 3 mm away from the cutting blade.

16. The shroud for a cutting blade of a power tool according to claim 15, wherein the third housing portion is configured to hold the at least one of the infrared detector or the thermocouple within non-contacting proximity to and no more than 2 mm away from the cutting blade.

17. The shroud for a cutting blade of a power tool according to claim 15, wherein the third housing portion is configured to hold the at least one of the infrared detector or the thermocouple within non-contacting proximity to and no more than 1 mm away from the cutting blade.

18. A method of operating a cast saw to cut a cast off of a patient, the method comprising the steps of:
   1) Providing the cast saw wherein the cast saw comprises:
      a) a cutting device having a temperature;
      b) a data generating module configured to generate data correlative to the temperature of the cutting device;
      c) a data collection and processing module which is configured to:
         i) collect the data correlative to the temperature of the cutting device, and
         ii) process the data correlative to the temperature of the cutting device to determine the temperature of the cutting device;
      d) a temperature notification module which is configured to:
         i) receive the temperature of the cutting device from the data collection and processing module,
         ii) produce a first temperature output corresponding to a safe temperature of the cutting device, and
         iii) produce a second temperature output corresponding to an excessive temperature of the cutting device, wherein the first output and the second output can be detected by a user of the cast saw;
      e) an ON/OFF switch;
   2) Detecting that the temperature notification module is producing the first temperature output and is not producing the second temperature output;
   3) Turning the ON/OFF switch to ON and operating the case saw to cut the cast;
   4) Turning the ON/OFF switch to OFF when the cast is completely cut.

19. The method according to claim 18, further comprising the step of:
   3a) turning the ON/OFF switch to FF when detecting that the temperature notification module is producing the second temperature output.

20. The method according to claim 19, further comprising the step of repeating steps 3) and 3a) until the cast is completely cut.

21. The method according to claim 18, wherein the temperature notification module is further configured to:
   iii) produce a third temperature output corresponding to a temperature of the cutting device higher than the safe temperature of the cutting device and lower than the excessive temperature of the cutting device.

22. The method according to claim 21, further comprising the step of turning the ON/OFF switch to OFF when detecting that the temperature notification module is producing the third temperature output.

23. The method according to claim 21, wherein the temperature notification module comprises at least one light emitting diode (LED) operable to produce a first color in response to the first temperature output, and a second color in response to the second temperature output.

24. The method according to claim 21, wherein the temperature notification module comprises a first light emitting diode (LED) operable to produce a first color in response to the first temperature output, a second LED operable to produce a second color in response to the second temperature output, and a third LED operable to produce a third color in response to the third temperature output.

25. The method according to claim 24, further comprising the step of turning the ON/OFF switch to OFF when detecting that the temperature notification module is producing the second temperature output or the third temperature output.

* * * * *